United States Patent
Tan et al.

(10) Patent No.: US 9,157,874 B2
(45) Date of Patent: Oct. 13, 2015

(54) SYSTEM AND METHOD FOR AUTOMATED X-RAY INSPECTION

(75) Inventors: Chun-Aun Tan, Penang (MY); Lee-Herng Cheah, Penang (MY)

(73) Assignee: VITROX CORPORATION BERHAD, Penang (MY)

( * ) Notice: Subject to any disclaimer, the term of this patent is extended or adjusted under 35 U.S.C. 154(b) by 524 days.

(21) Appl. No.: 13/545,715

(22) Filed: Jul. 10, 2012

(65) Prior Publication Data

US 2013/0230144 A1 Sep. 5, 2013

(30) Foreign Application Priority Data

Mar. 2, 2012 (MY) .............................. PI201200968

(51) Int. Cl.
*G01N 23/04* (2006.01)

(52) U.S. Cl.
CPC ........ *G01N 23/046* (2013.01); *G01N 2223/419* (2013.01)

(58) Field of Classification Search
CPC ........... G01N 23/046; G01N 2223/419; G01B 11/2522
USPC ............................................................ 378/63
See application file for complete search history.

(56) References Cited

U.S. PATENT DOCUMENTS

| | | | |
|---|---|---|---|
| 5,867,604 A * | 2/1999 | Ben-Levy et al. | 382/254 |
| 6,040,910 A * | 3/2000 | Wu et al. | 356/613 |
| 6,577,405 B2 * | 6/2003 | Kranz et al. | 356/601 |
| 7,525,669 B1 * | 4/2009 | Abdollahi | 356/603 |
| 2003/0114996 A1* | 6/2003 | Ragland | 702/35 |
| 2003/0137673 A1* | 7/2003 | Cox et al. | 356/601 |
| 2008/0117438 A1* | 5/2008 | Quirion et al. | 356/610 |

* cited by examiner

Primary Examiner — Michael Maskell
(74) Attorney, Agent, or Firm — Mannava & Kang, P.C.

(57) ABSTRACT

An automated X-ray inspection system employing phase shift profilometry (PSP) and three dimensional (3D) surface modeling for improving inspection of an object, includes at least one projector for projecting light to the object, at least one optical lens for imaging a light pattern obtained from the object to at least one camera, the at least one camera being adapted to capture a plurality of images of the object. The light passing from the projector lens of the at least one projector illuminates the object thereby generating the light pattern to be imaged from the object to the at least one camera via the at least one optical lens.

27 Claims, 6 Drawing Sheets

SYSTEM AND METHOD FOR AUTOMATED X-RAY INSPECTION

BACKGROUND OF THE INVENTION

1. Field of the Invention

Embodiments of the present invention relate to inspection systems, and more particularly, to automated x-ray inspection systems and corresponding methods.

2. Description of the Related Art

It is well known fact that during the assembly of some products, it is necessary to inspect the product at a stage in the assembly when the elements to be inspected are hidden from the human eye or a machine vision inspection system. Currently, the reduced size of one or more electronics components and the consequent increased density of items on printed circuit boards (PCBs) have caused the traditional ways of inspection to be no longer sufficient for an affordable and precise quality control inspection. Moreover, printed circuit boards are now produced in large quantities, and as they are expensive and are used in expensive equipment, it is important that they be produced accurately, with minimum wastage. Unfortunately, because of the manufacturing methods available, wastage because of rejects is still higher than in other industries. Furthermore, where a Direct Chip Attached (DCA) technology is used, in which the solder connections are hidden from view, fast accurate quality control inspection of the electronic devices is very difficult.

Currently, the V810's system architecture doesn't have the capability to measure the actual board height. Although existing autofocus including profile analyzer technique can estimate the correct solder slice for most of the joint types, it fails in cases where the joint for the inspection has large and thick neighboring components for e.g. tall capacitor, multilayer on one side and also when the joint or pad is thin.

Currently in the art, the PCB is scanned with a camera utilizing telecentric lenses, which views in parallel beam imaging to photograph a section of the board, and use software to analyze the image and in other cases the PCB is scanned with a camera utilizing fixed-focus lens. However, there remains a problem with this arrangement in which imaging camera is only focusing sharply within certain depth of field (DOF). Moreover, one or more objects that fall out of this range are blur and is out of machine's inspectability. Furthermore, there is a disadvantage with this arrangement in that the camera can only view the image in two directions, which is not a problem as long as the board is exactly flat, but although normally these boards are nominally flat, exact flatness is difficult, if not impossible to achieve for various reasons. Steps are taken to keep the board flat to the degree necessary to make the method accurate, but this is not easy, and in fact the board is sometimes clamped in an effort to keep it sufficiently flat to make the results acceptable. It should be borne in mind at this time that the dimensions of the degree of out of flatness (i.e. warpage) of the board which are involved are measured in microns, but even warpage of the board to this minute degree can have a serious effect on the accuracy of the inspection.

In one or more cases, penetrating radiation is employed to inspect products by producing images of the internal structure of the devices and the connections. Particularly, the solder joints that are located under the body of a component would not normally be visible but can be observed via X-ray inspection. Currently, most of the existing inspection systems use X-ray radiations and radiographic techniques. For example, the solder joints attaching some high density integrated circuits to a circuit board may be inspected only after the integrated circuits are in place covering the joints to be inspected. In mode of operation, an X-ray inspection system may be employed, which may include an X-ray source, opposing a detector about the part to be inspected. The X-ray source is normally an electron tube accelerating electrons in vacuum from a cathode to a fixed anode as focused by one or more grids. The X-ray radiation penetrates any obscuring structure to produce a shadow image or radiograph of the part from which the desired elements may be discerned as variations in X-ray attenuation. For example, a metallic solder joint may be detected as a region of high attenuation contrasting with the uniform and frequently lesser attenuation of the obscuring integrated circuit package and die.

Additionally, a rigid mounting of the X-ray source may be employed to reduce any physical shock to the X-ray source which may adversely affect the size of the X-ray source's focal spot. Thermal variations are reduced by leaving the X-ray source on at all times. The small focal spot of the X-ray source (less than one-hundredth the diameter of a typical medical X-ray source) is necessary to eliminate a penumbra that may blur a highly magnified image and is accomplished by multiple grids and a special X-ray source anode geometry.

However, while employing automated X-ray inspection (AXI) knowledge of the surface where solder joint are mounted to the printed circuit board (PCB) is important for classification. Inspection machine's call rate and accuracy is very much dependent on it. This information can be obtained either directly by surface height profile measurement or indirectly by calculating the image sharpness matrixes. However, both approaches are not perfect. Moreover, the direct surface height profile mapping cannot measure joints that are hidden from sight while the indirect software approach is not reliable for certain joint types. Furthermore, the current available AXI machine, implement the indirect approach.

Moreover, 3-D scanning laser mapping is slow due to the time required to obtain and process the 3D laser scan data. Furthermore, in 3-D scanning laser mapping in Agilent's 5DX machine (AXI) system height information is collected point by point and in other scenarios utilize line scanning. Consequently, the scanning speed became speed bottleneck to the 5DX system. In addition, setup time for laser mapping is also tedious with poor repeatability. The focused laser spot used in the measurement is bright and it tends to saturate the camera easily when the spot fall on copper traces (PCB) or high reflective component leads. Moreover, this information is not stored in CAD (NDF) files and they must be chosen carefully by the end users. In practice, the number of points required is more than hundreds per board, i.e. setting up a PCB during test development can be very time consuming and painstaking.

Furthermore, in any optical metrology that involves moiré and phase shift profilometry techniques are usually faster but they are normally used for measurements that are related to surface deformations. The surface deformations include height measured with respect to its neighboring objects in a continuous manner, for e.g. a human face or components on board and not absolute height measurement.

There remains a need in the art for a method to improve system call rate and test coverage for the automated x-ray inspection (AXI) machine. Henceforth, there exists a need in the art for a method and system to reduce false call and false rejects in automated x-ray inspection (AXI) machine.

SUMMARY OF THE INVENTION

Embodiments of the present disclosure disclose, a method for improving inspection of an object by an automated X-ray inspection system employing phase shift profilometry (PSP) and three dimensional (3D) surface modeling, includes the steps of projecting light from at least one projector to the object, imaging a light pattern obtained from the object by employing at least one optical lens to at least one camera for capturing a plurality of images of the object. Particularly, the light passing from the projector lens of the at least one projector illuminates the object thereby generating the light pattern to be imaged from the object to the at least one camera via the at least one optical lens Embodiments of the present disclosure disclose, a method for integrating phase shift profilometry (PSP) to an automated X-ray inspection system for improving inspection of an object by three dimensional (3D) surface modeling including the steps of performing automated x-ray inspection of the object in production mode and calibrating a x-ray camera, determining at least one region of interest (ROI) of the object for phase shift profilometry (PSP) for generating surface mapping of the object, collecting multiple images projected from the object, evaluating a sharpness matrix of multiple reconstructed slice images of the object, computing a solder joint reference plane of the object from the evaluated sharpness matrix, providing a complete surface profile of the object for reconstructing and generating multiple 3D image slices by utilizing tomosynthesis and inspecting the object for at least one joint and component of the object.

Embodiments of the present disclosure disclose, an automated X-ray inspection system employing phase shift profilometry (PSP) and three dimensional (3D) surface modeling for improving inspection of an object. The system includes at least one projector for projecting light to the object, at least one optical lens for imaging a light pattern obtained from the object to at least one camera. Particularly, light passing from the projector lens of the at least one projector illuminates the object thereby generating the light pattern to be imaged from the object to the at least one camera via the at least one optical lens.

The foregoing objectives of the present invention are attained by employing and incorporating phase-shift profilometry (PSP) to AXI machine. Particularly, the automated X-ray inspection system employs phase shift profilometry (PSP) and three dimensional (3D) surface modeling for improving inspection of an object.

In accordance with one aspect of the present invention, the method may further include the step of calibrating a plurality of parameters of the object by a calibration plate and evaluating height information associated with the object by a 3D surface interpolator and generating a complete surface profile of the object. Particularly, the plurality of parameters includes height, position, magnification and the like.

In accordance with another embodiment of the present invention, the method may further include the steps of mapping surface height of the at least one region of interest (ROI) of the object by phase shift profilometry (PSP), acquiring optical image of the plurality of images by an optical image acquisition, computing height of the object along z-axial direction, determining the complete surface profile of the object, determining a single point and/or multiple points per field of view (FOV) of the object, correcting at least one image perspective of the plurality of images of the object and providing a measured surface profile of the at least one object for the at least one region of interest (ROI) to a 3D surface interpolator for interpolation and generating a global board warpage matrix.

In accordance with one aspect of the present invention, the system further includes a calibration plate for calibrating multiple parameters of the object and a 3D surface interpolator to evaluate height information associated with the object. Moreover, the 3D surface interpolator generates a partial and/or complete surface profile of the object. Furthermore, the multiple parameters include height, position, magnification and the like.

In accordance with one aspect of the present invention, the surface interpolator is a global surface model (GSM) to inspect the object and the global surface model (GSM) use a thin-plate spline (TPS) method for evaluating surface interpolation of the object.

In accordance with another aspect of the present invention, the surface interpolator is a Local Surface Model (LSM) to inspect the object and the Local Surface Model (LSM) use Predictive Slice Height (PSH) to estimate a z-height of at least one of a particular joint and solder of the object by taking an average z-height value of all its close neighbor focused joints for evaluating surface interpolation of the object.

In accordance with one aspect of the present invention, the at least one projector is configured to project a fringe pattern to the object.

In accordance with another aspect of the present invention, the at least one projector is configured to project a structured white light pattern to the object.

In accordance with one aspect of the present invention, the at least one projector is a Pico Projector or equivalent means. Moreover, the at least one pica-projector is implemented by DLP (digital light processing) technology.

In accordance with one aspect of the present invention, the at least one optical lens includes a telecentric lens.

In accordance with one aspect of the present invention, means for focusing are arranged telecentrically with respect to the structured white light pattern.

In accordance with one aspect of the present invention, the means for focusing are a fixed focal length operative to provide at least one image of structured white light pattern from the object to the at least one camera.

In accordance with one aspect of the present invention, the system further includes a data processing device for computing multiple phase shift values of the object with respect to a reference plane. The data processing device includes a memory to collect the multiple phase shift values of the object and a processor includes at least one module to determine and measure surface profile of at least one object for multiple preselected regions.

In accordance with one aspect of the present invention, the measured surface profile of the at least one object for the multiple preselected regions is provided to the 3D surface interpolator for interpolation and generating a global board warpage matrix.

In accordance with one aspect of the present invention, the complete surface profile of the object is provided for reconstructing and generating multiple 3D image slices by utilizing tomosynthesis.

In accordance with another aspect of the present invention, the 3D surface interpolator handle local surface model too. The partial surface profile of the object is modeled.

In accordance with one aspect of the present invention, the object is a printed circuit board (PCB) and the at least one camera operates in line scan mode or area scan mode.

In accordance with another object of the present invention to provide an automated X-ray inspection system employing phase shift profilometry (PSP) and three dimensional (3D) surface modeling for improving inspection of an object includes at least one optical lens including a fixed-focus lens for imaging a light pattern obtained from the object to at least one camera, the at least one camera being adapted to capture multiple images of the object, a processing system in communication with the 3D scanner to receive the multiple images and data representative of a surface of the object. The processing system generating a textured 3D model of the object from the multiple images and data representative of the surface of the object. Moreover, the processing system maps textures from the multiple images to corresponding points in a 3D model, each visible point in the 3D model corresponding to a texture from one of the multiple images and a light source of the 3D scanner including a laser light source.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Various embodiments of the present invention provide an automated X-ray inspection system employing phase shift profilometry (PSP) and three dimensional (3D) surface modeling for improving inspection of an object. The present invention is aimed to focus inconsistency and inaccuracy in automated X-ray inspection (AXI) machine. More specifically, the present invention includes wider machine's test coverage because of better focus accuracy. Subsequently, more consistency can be achieved at previously hard to focus and inspect multiple joint types. Moreover, the present invention provides much faster inspection method and has a potential to evolve and provide broad radiation spectrum coverage optical plus x-ray 3D inspection system.

Figure 1:
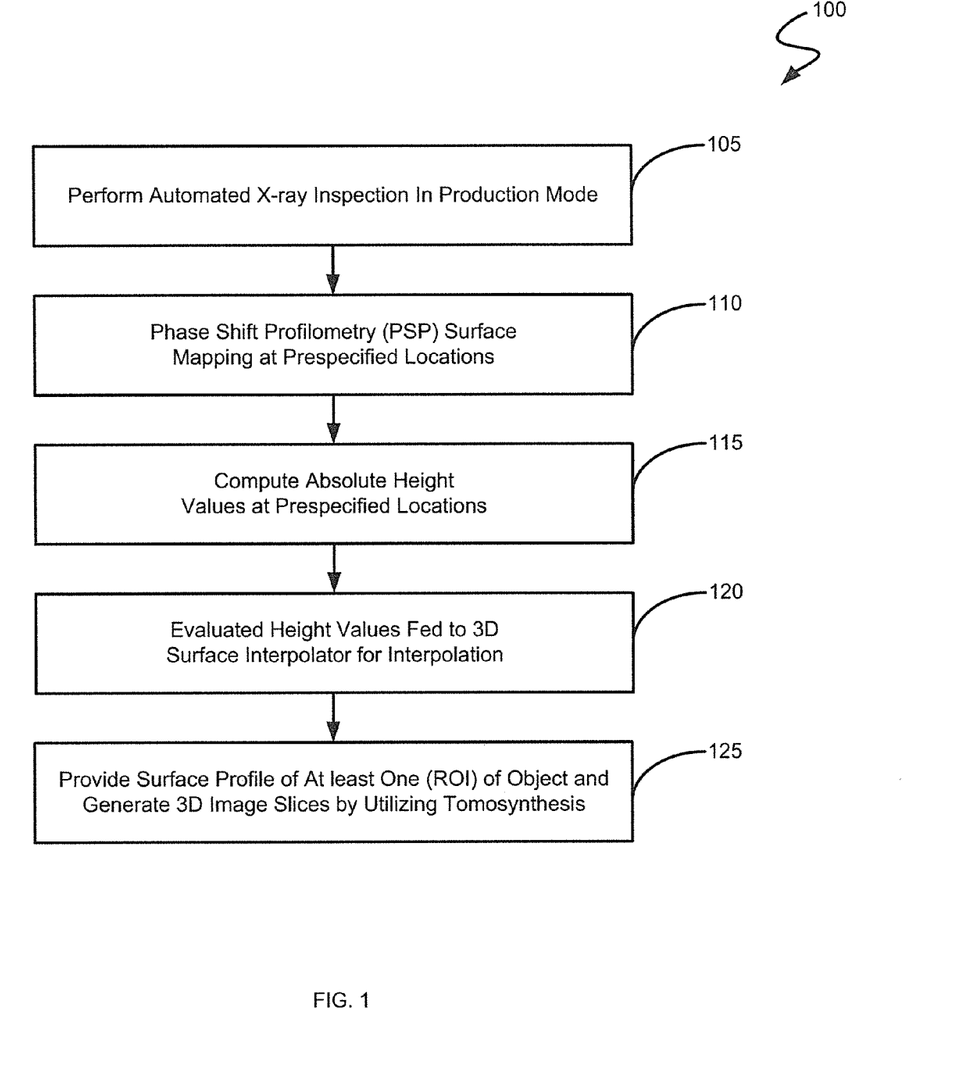
FIG. 1 is a flow diagram illustrating a method for improving inspection of an object by an automated X-ray inspection system employing phase shift profilometry (PSP) and three dimensional (3D) surface modeling, according to one embodiment of the present invention.
Figure 5A:
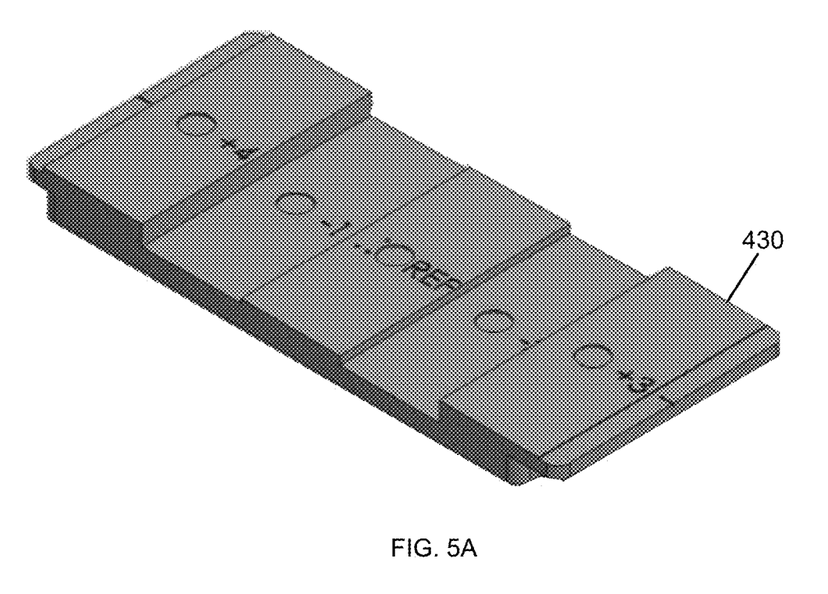
FIG. 5A is a perspective view of a calibration plate, according to an embodiment of the present invention.
Figure 5B:
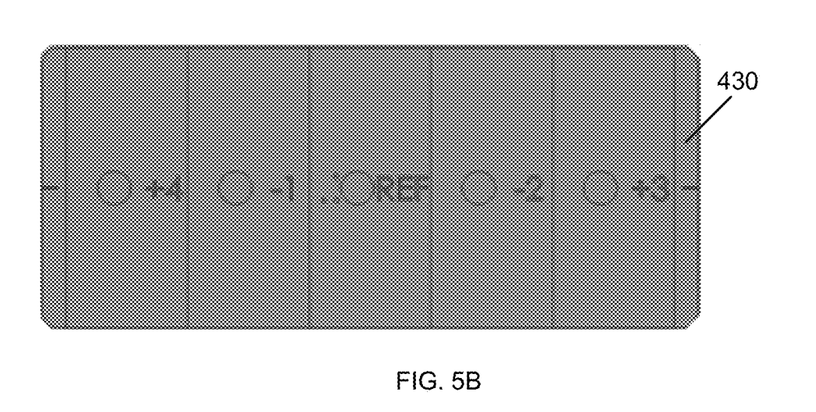
FIG. 5B is a top view of the calibration plate, according to an embodiment of the present invention.
Figure 5C:
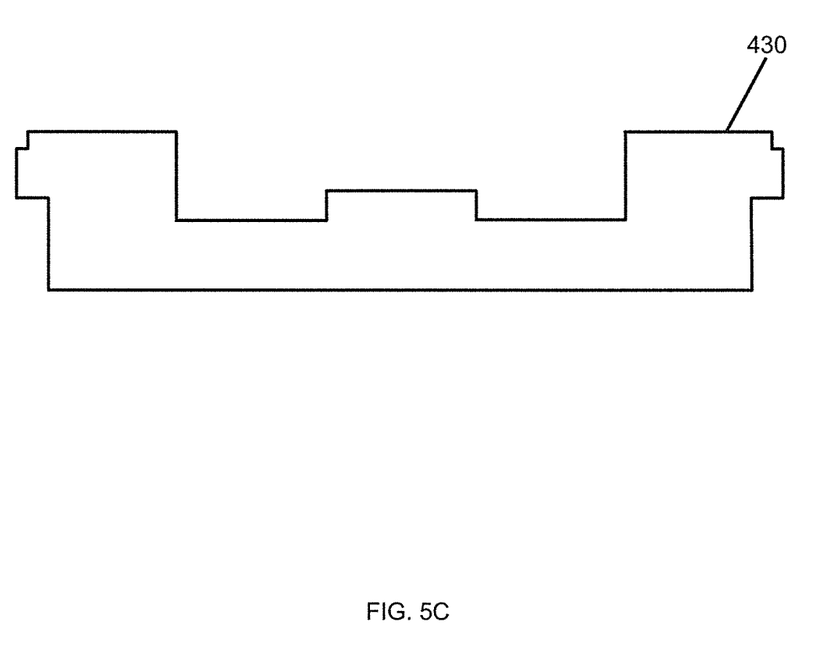
FIG. 5C is a front view of the calibration plate, according to an embodiment of the present invention.

FIG. 1 is a flow diagram 100 illustrating a method for improving inspection of an object by an automated X-ray inspection system employing phase shift profilometry (PSP) and three dimensional (3D) surface modeling, according to one embodiment of the present invention. At step 105, the printed circuit board (PCB) is loaded to automated X-ray inspection system for inspecting the PCB in production mode. Particularly, light is projected from at least one projector to the PCB and a light pattern is obtained. Moreover, the one or more x-ray cameras are calibrated with known calibration apparatus available in the art and associated software. FIG. 5A is a perspective view, FIG. 5B is a top view and FIG. 5C is a front view of a calibration plate 430, according to an embodiment of the present invention. The calibration plate 430 utilized in the present invention performs height, position and magnification calibration. The light pattern from the PCB is obtained by employing at least one optical lens and the light pattern is imaged to the at least one camera for capturing a plurality of images of the PCB. Moreover, the light passing from a projector lens of the at least one projector illuminates the PCB thereby generating the light pattern to be imaged from the PCB to the at least one camera via the at least one optical lens. At step 110, the phase shift profilometry (PSP) surface mapping of the PCB is performed for one or more pre-specified locations of the PCB. In mode of operation, a light pattern is projected onto a surface of the one or more pre-specified locations of the PCB and multiple images of the pre-specified locations of the PCB are captured by the at least one camera for optical image acquisition.

In accordance with an embodiment of the present invention, the at least one projector is configured to project a structured white light pattern to the PCB. Particularly, the at least one projector is a Pico Projector or equivalent means. Moreover, the one or more pico-projectors are implemented by DLP (digital light processing) technology.

In accordance with another embodiment of the present invention, the at least one projector is configured to project a fringe pattern to the PCB.

At step 115, the absolute height values at the one or more pre-specified locations of the PCB are computed. The phase-shifted images of the one or more pre-specified locations of the PCB are captured to measure height of features of the PCB. At step 120, the evaluated surface profile of the at least one PCB for the multiple preselected regions is provided to the 3D surface interpolator for interpolation. Particularly, the evaluated height information associated with the PCB is fed to the 3D surface interpolator for interpolation and a global board warpage matrix is generated. In operation, one or more separate regions of the object may be inspected. Each separate region has one surface model. However, the region of interest (ROI) of the object may be dragged and expanded from a single field of view (FOV) i.e. having the smallest region of interest (ROI) to the whole board employing a global surface model (GSM) to inspect the object. Particularly, the global surface model (GSM) for interpolating surfaces over scattered data use a thin-plate spline (TPS) algorithm as the mathematical foundation for evaluating the surface interpolation. The TPS model for interpolating surfaces over scattered data is based on minimum physical bending energy of a thin metal plate on point constraints instead of pure surface interpolation. At step 125, the complete surface profile of the object is provided for reconstructing and generating multiple 3D image slices by utilizing tomosynthesis. Particularly, the object is the printed circuit board (PCB). Consequently, a three-dimensional map of the PCB is constructed by utilizing at least one profile slice. Particularly, in case of good or poor solder joint classification, the users are only interested in one or more slice images. For e.g. in ball grid array (BGA) inspection a good or bad joint is only decided from three image slices including pad, mid and package.

In accordance with another embodiment of the present invention, the height data evaluated from the PSP and z-height selector are fed to 3D surface interpolator.

Figure 2:
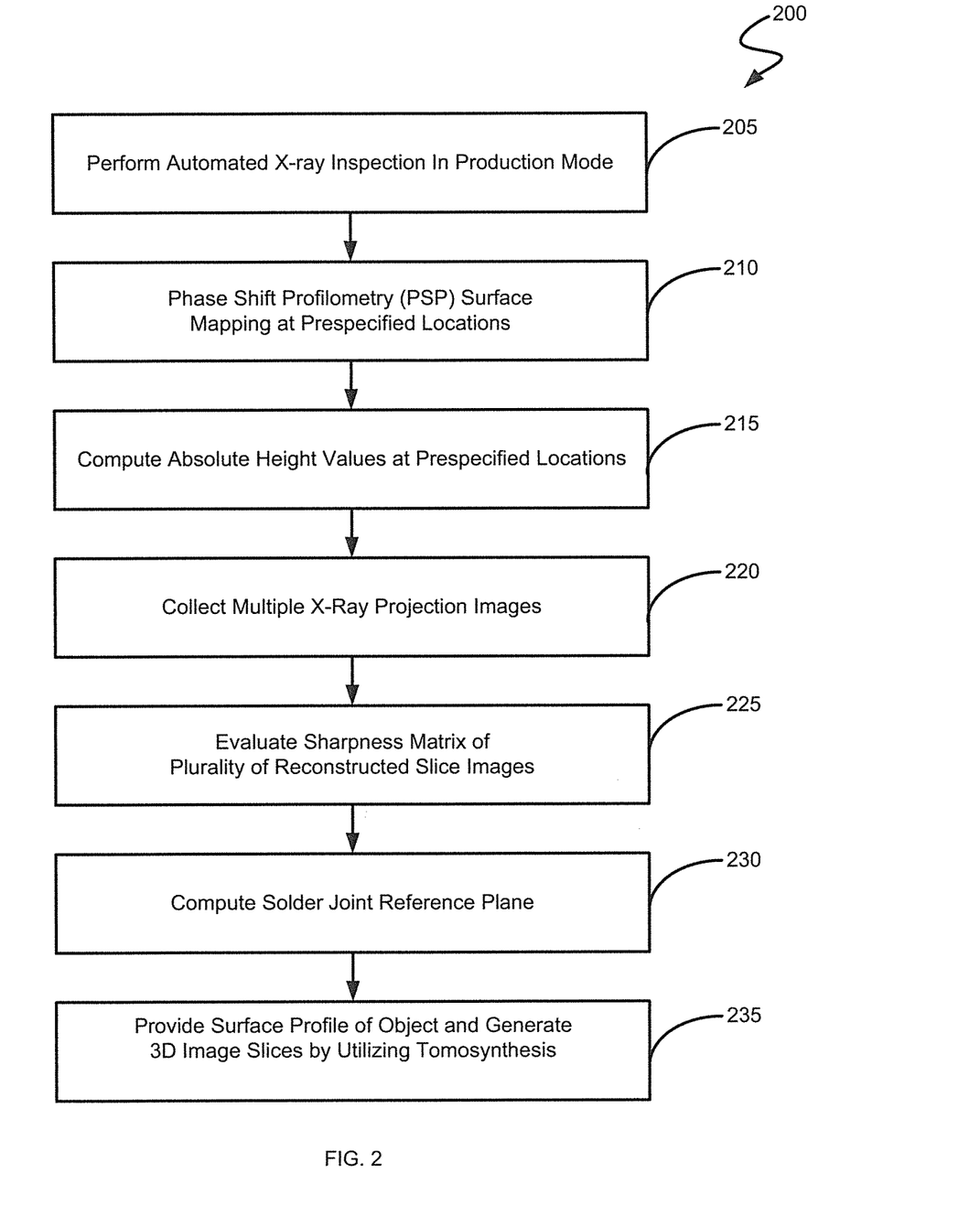
FIG. 2 is a flow diagram illustrating a method for improving inspection of an object by an automated X-ray inspection system employing phase shift profilometry (PSP) and three dimensional (3D) surface modeling, according to another embodiment of the present invention.

FIG. 2 is a flow diagram 200 illustrating a method for improving inspection of an object by an automated X-ray inspection system employing phase shift profilometry (PSP) and three dimensional (3D) surface modeling, according to another embodiment of the present invention. At step 205, the printed circuit board (PCB) is loaded to the automated X-ray inspection system for inspecting the PCB in production mode. Particularly, light is projected from at least one projector to the PCB and the light pattern is obtained. Moreover, the one or more x-ray cameras are calibrated. At step 210, the phase shift profilometry (PSP) surface mapping of the PCB is performed for one or more pre-specified locations of the PCB. In mode of operation, the light pattern is projected onto the surface of the one or more pre-specified locations of the PCB and multiple images of the pre-specified locations of the PCB are captured by the at least one camera for optical image acquisition. At step 215, the absolute height values at the one or more pre-specified locations of the PCB are computed. At step 220, multiple x-ray projected images are collected. At step 225, a sharpness matrix of the multiple reconstructed slice images of the PCB are evaluated. At step 230, a solder joint reference plane is computed indirectly from the evaluated sharpness matrix. At step 235, a complete surface profile of the PCB is provided for reconstructing and generating multiple 3D image slices by utilizing tomosynthesis and inspecting the PCB for at least one joint and component of the PCB. Those of ordinary skill will appreciate that at step 235, at least one partial profile of the complete surface profile of the PCB may also be provided for reconstructing and generating multiple 3D image slices by utilizing tomosynthesis and inspecting the PCB for at least one joint and component of the PCB.

Figure 3:
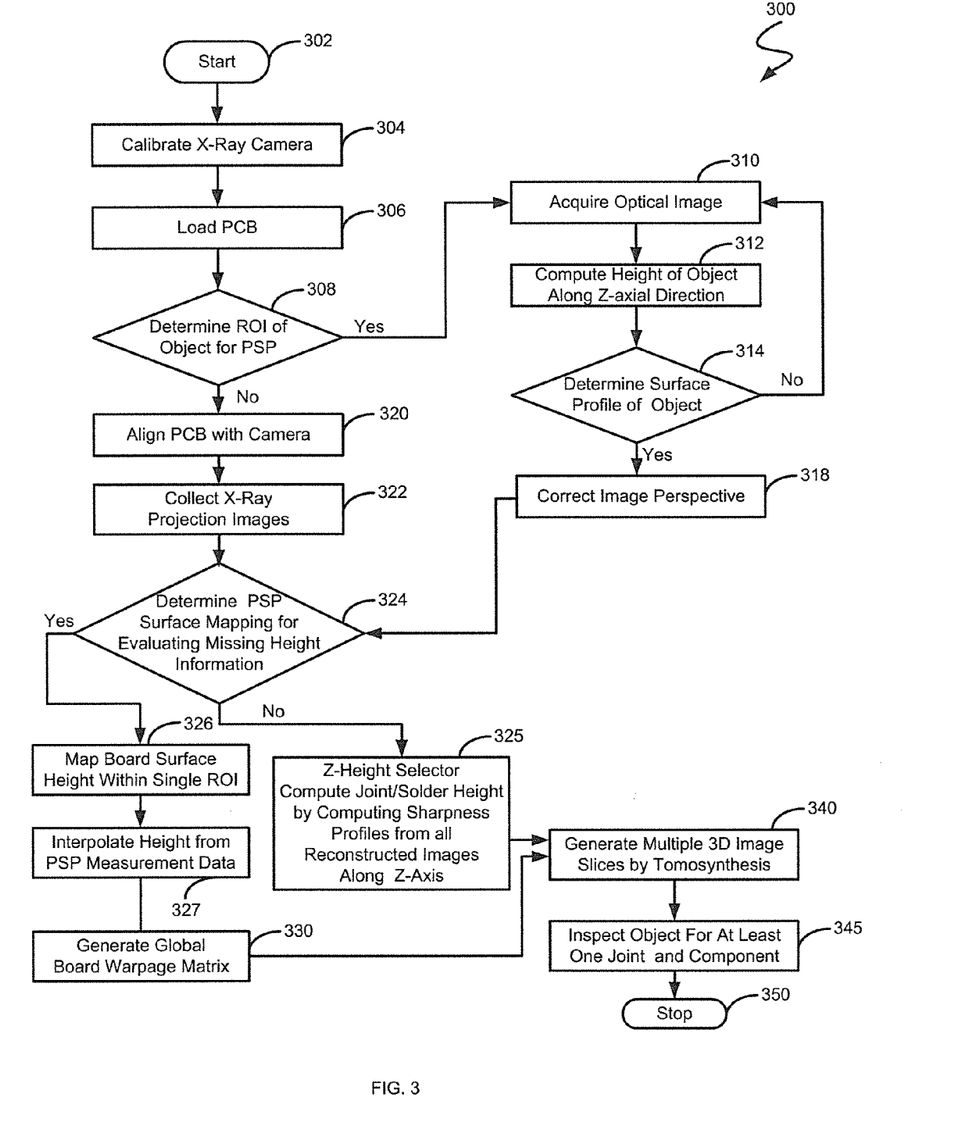
FIG. 3 is a flow chart illustrating a method for improving inspection of an object by an automated X-ray inspection system employing phase shift profilometry (PSP) and three dimensional (3D) surface modeling, according to one embodiment of the present invention.

FIG. 3 is a flow chart 300 illustrating a method for improving inspection of an object by an automated X-ray inspection system employing phase shift profilometry (PSP) and three dimensional (3D) surface modeling, according to one embodiment of the present invention. The method for improving inspection of the PCB by the automated X-ray inspection system starts at step 302 and proceeds to step 304. At step 304, at least one camera is calibrated. Particularly, the at least one camera captures multiple images of the PCB.

In accordance with another embodiment of the present invention, the at least one camera is employed for determining capacitor polarity. It will be appreciated that the at least one camera may be a phase shift profilometry (PSP) optical camera, an x-ray camera and the like.

At step 306, the PCB is loaded on the automated X-ray inspection system for inspection. At step 308, a determination is made as to whether or not to perform phase shift profilometry (PSP) of at least one region of interest (ROI) of the PCB for generating surface mapping of the PCB. If phase shift profilometry (PSP) is to be performed for the at least one region of interest (ROI) of the PCB and the determination at step 308 is "YES" the method 300 proceeds to step 310. At step 310, multiple images are acquired for optical image acquisition to acquire optical image of the at least one region of interest (ROI) of the PCB. At step 312, height of the at least one preselected region of interest (ROI) of the PCB is computed along z-axial direction. Particularly, adjusted x and y pixel coordinates are converted with updated runtime alignment matrix. Generally, the adjustment in x and y coordinates includes an x-ray alignment matrix, primarily for compensating the rotation of the PCB with a geometrical transformation, followed by position calibration of the PSP optical camera for correlating the camera to the x-ray imaging coordinates system by employing a calibration plate 430. It will be appreciated that the geometrical transformation may be an affine transformation. Subsequently, the reconstructed region focus profile is modified. At step 314, a determination is made as to whether or not complete surface profile of the PCB is determined. If complete surface profile of the PCB is not determined by phase shift profilometry (PSP) and the determination at step 314 is "NO" the method 300 proceeds to step 310.

If partial surface profile and/or complete surface profile of the PCB are determined by phase shift profilometry (PSP) and the determination at step 314 is "YES" the method 300 proceeds to step 318.

At step 318, the image perspective of the one or more images of the multiple images of the PCB is corrected. The one or more image perspective is corrected that is due to different magnification factors along an optical axis. Moreover, the one or more corrections were only carried out for one or more selected points and not the whole field of view (FOV) of the object. The method 300 proceeds from step 318 to step 324.

In accordance with one embodiment of the present invention, if phase shift profilometry (PSP) is not performed for the at least one region of interest (ROI) of the PCB and the determination at step 308 is "NO" the method 300 proceeds to step 320. At step 320, the PCB is aligned with the one or more x-ray cameras along an optical axis by effecting the required movements to the worktable on which the PCB is secured. At step 322, the multiple images projected from the PCB are collected.

At step 324, a determination is made as to whether or not phase shift profilometry (PSP) surface mapping to evaluate missing height information of the object should be performed. The missing height information of the PCB is evaluated by providing available board height information of the PCB to the 3D surface interpolator for interpolation. If phase shift profilometry (PSP) surface mapping to evaluate missing height information of the object is performed and the determination at step 324 is "YES" the method 300 proceeds to step 326. At step 326, the present invention utilize the phase shift profilometry (PSP) surface mapping to map the board surface height within a single Region of interest (ROI). At step 327, in accordance with one embodiment of the present invention, the surface interpolator employed in the PSP may include a Thin-Plate Spline (TPS) method and may be extended from one field of view (FOV) to the full PCB board. The Global Surface Model (GSM) of the present invention is built from the Thin-Plate Spline (TPS) method. Particularly, the Thin-Plate Spline (TPS) method is applied to every Region of interest (ROI). Consequently, the height of the solder and/or joint of the PCB is interpolated from the PSP measurement data. Moreover, one or more pre-specified points are used as an input for evaluating the height of the solder and/or joint of the PCB. However, when PSP is not employed the Global Surface Model (GSM) wouldn't be activated. Furthermore, applying the Thin-Plate Spline (TPS) method to every Region of interest (ROI) provides more flexibility. The method 300 proceeds from step 327 to step 330. At step 330, a global board warpage matrix is generated. The method 300 proceeds to step 340.

In accordance with another embodiment of the present invention, if phase shift profilometry (PSP) surface mapping to evaluate missing height information of the object is not performed and the determination at step 324 is "NO" the method 300 proceeds to step 325. At step 325, the height of the solder and/or joint of the PCB is computed by the autofocus (profile analyzer) by computing sharpness profiles from all reconstructed images along the z-axis. Particularly, the Z-Height selector of the present invention includes the autofocus (profile analyzer), the Predictive Slice Height (PSH) and the Reference From Plane (RFP). However, the Reference From Plane (RFP) is used when the board's physical variations like board thickness and warpage are insignificant. Moreover, one of the surface interpolators used in the present invention is a Local Surface Model (LSM) to inspect the PCB and the Local Surface Model (LSM) use Predictive Slice Height (PSH) to estimate a z-height of at least one of a particular joint and solder of the PCB by taking an average z-height value of all its close neighbor focused joints for evaluating surface interpolation of the PCB. Particularly, the Predictive Slice Height (PSH) assumes that all the points stay in one plane. Since, the Predictive Slice Height (PSH) is utilized for a small local area it is consequently known as Local Surface Model in the present invention. Moreover, PSH is used to estimate the difficult to focus joint slice height from its neighboring focused joints. In operation, the Z-Height selector is integrated and grouped together with the PSP and GSM modules under the Z-Height Locator in the present invention. The method 300 proceeds to step 340. At step 340, the evaluated values are fed to tomosynthesis reconstruction engine to generate multiple 3D slices. At step 345, the loaded PCB is inspected for one or more solder joints and components of the PCB. At step 350, the method 300 ends.

Figure 4:
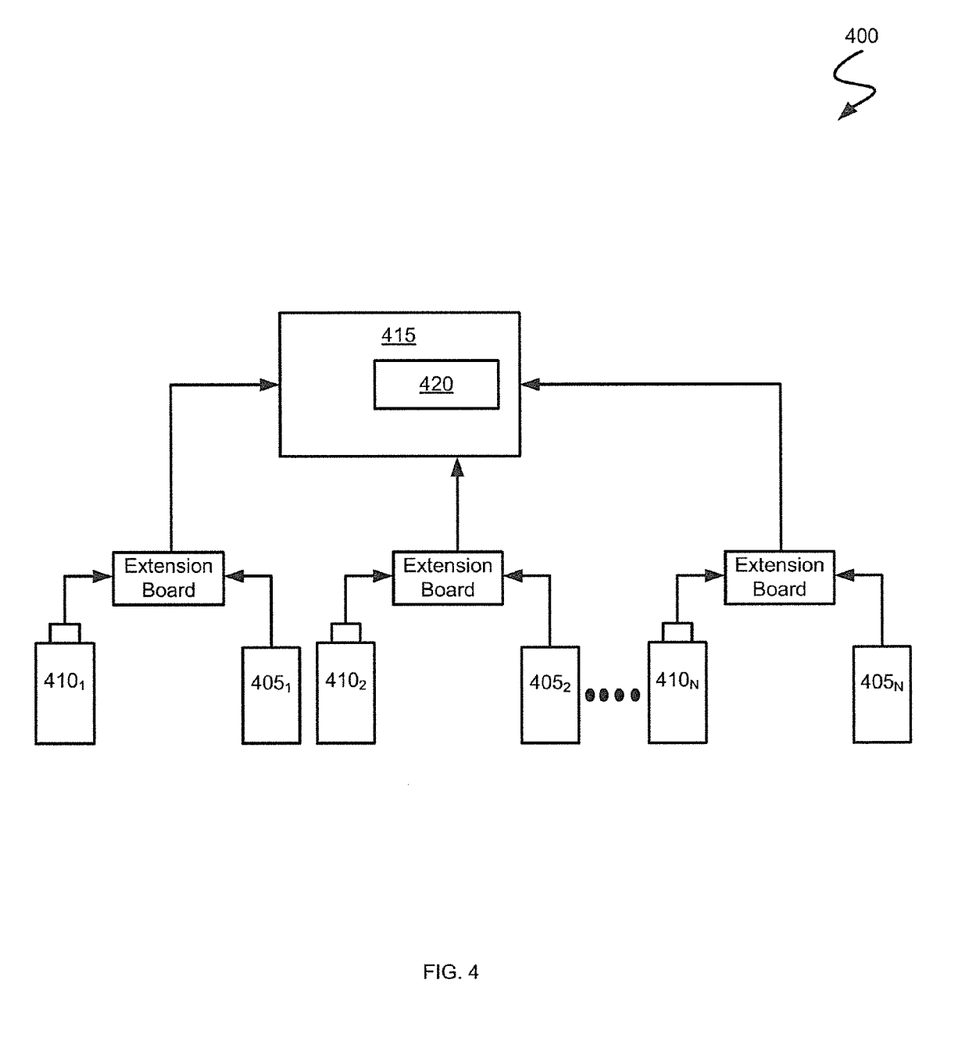
FIG. 4 is a schematic illustration of the phase shift profilometry (PSP) system, according to one embodiment of the present invention.

FIG. 4 is a schematic illustration of the phase shift profilometry (PSP) system 400, according to one embodiment of the present invention. The automated X-ray inspection system employing phase shift profilometry (PSP) and three dimensional (3D) surface modeling for improving inspection of the PCB includes at least one projector $405_1, \ldots, 405_N$ for projecting light to the PCB. The at least one projector $405_1, \ldots, 405_N$ includes a projector lens. Particularly, light passing from the projector lens of the at least one projector $405_1, \ldots, 405_N$ illuminates the PCB thereby generating the light pattern to be imaged from the PCB to the at least one camera $410_1, \ldots, 410_N$ via the at least one optical lens. In mode of operation, the at least one optical lens images the light pattern obtained from the PCB to at least one camera $410_1, \ldots, 410_N$. Particularly, the at least one projector is a Pico Projector or equivalent means. Moreover, the one or more pico-projectors are implemented by DLP (digital light processing) technology. In a DLP based projector, images are produced by DMDs (Digital Micromirror Devices). DMD is an optical semiconductor on which the DLP projection technology is based. A surface of a DMD chip has several hundred thousand microscopic mirrors arranged in a rectangular array which correspond to the pixels in the image to be displayed. In the DLP projector, the image is created by microscopically small mirrors laid out in a matrix on a semiconductor chip (DMD). Each mirror represents one or more pixels in the projected image. Particularly, light passing from the projector lens of the at least one projector illuminates the PCB thereby generating the light pattern to be imaged from the PCB to the at least one camera $410_1, \ldots, 410_N$ via the at least one optical lens. Moreover, the at least one camera $410_1, \ldots, 410_N$ is adapted to capture multiple images of the PCB. Furthermore, in order to pack the one or more PSP modules in the present system, the pico digital light processing (DLP) projector, ultra compact lenses and camera are employed in the present invention.

In accordance with one embodiment of the present invention, the one or more cameras $410_1, \ldots, 410_N$ operate in line scan mode or area scan mode.

In accordance with one embodiment of the present invention, the system of the present invention further includes the calibration plate 430 for calibrating multiple parameters of the PCB and the 3D surface interpolator to evaluate height information associated with the PCB. Consequently, the system generates a partial or complete surface profile of the PCB. Particularly, the multiple parameters include height, position, magnification and the like.

In accordance with one embodiment of the present invention, the system 400 further includes a data processing device 415 for computing multiple phase shift values of the PCB with respect to a reference plane. The data processing device 415 includes a memory to collect the multiple phase shift values of the PCB and a microcontroller 420 includes at least one module to determine and measure surface profile of at least one PCB for multiple preselected regions. In mode of operation, the measured surface profile of the at least one PCB for the multiple preselected regions is provided to the 3D surface interpolator for interpolation. Consequently, a global board warpage matrix is generated. Further, the complete surface profile of the PCB is provided for reconstructing and generating multiple 3D image slices by utilizing tomosynthesis.

In accordance with another embodiment of the present invention, the 3D surface interpolator may be stored as a set of instructions in the data processing device 415. In operation, the set of instructions when executed by the data processing device 415 performs the interpolation. It should be appreciated in the art that one or more set of instructions may be stored in the data processing device 415 which when executed performs one or more functions required by the automated X-ray inspection system of the present invention.

In accordance with another embodiment of the present invention, the automated X-ray inspection system employing phase shift profilometry (PSP) and three dimensional (3D) surface modeling for improving inspection of the PCB includes at least one optical lens including a fixed-focus lens for imaging a light pattern obtained from the PCB to at least one camera. The at least one camera being adapted to capture multiple images of the PCB and a processing system in communication with the 3D scanner to receive the multiple images and data representative of a surface of the PCB. Particularly, the processing system generates a textured 3D model of the printed circuit board (PCB) from the multiple images and data representative of the surface of the PCB. Moreover, the processing system maps one or more textures from the multiple images to corresponding points in a 3D model. Furthermore, each visible point in the 3D model corresponds to a texture from one of the multiple images. The light source of the 3D scanner includes a laser light source.

As discussed previously, the one or more cameras employed are compact cameras. In the preferred embodiment of the present invention, compact fixed focal length lenses are employed in the present invention.

In accordance with an embodiment of the present invention, the at least one optical lens includes a telecentric lens. The telecentric lens is configured to improve the uniformity of the light or image field and/or to improve the optical access to the edge surfaces. As will be appreciated by those skilled in the art, a telecentric lens system makes all views to the surface substantially parallel.

In accordance with an embodiment of the present invention, means for focusing are arranged telecentrically with respect to the structured white light pattern. Particularly, the means for focusing are a fixed focal length operative to provide at least one image of structured white light pattern from the PCB to the at least one camera.

Therefore, as may be seen, various embodiments of the present invention are aimed at to provide methods and systems to improve call rate, test coverage, reduce false call and false rejects in AXI machine, as described hereinabove. Particularly, the combination of PSP technique in existing AXI platform and 3D surface model increases the call rate, test coverage and also the inspection accuracy. The 3D surface interpolator of the present invention evaluates missing height information of the PCB.

Henceforth, various embodiments of the present invention provide more accurate and robust methods and systems as compared to the conventional technologies. By employing various embodiments of the present invention, it is possible to achieve near real-time inspection. As explained above, the thin-plate splines model is derived from physical basis, and hence the interpolated height values are more reliable and accurate even with relatively scarce height data (probably ~4 data per $cm^2$), which allows it to extend from one field of view (FOV) to full board interpolation.

Moreover, the present invention inspects the put-through hole (PTH) board which most of current AXI system (except Agilent's legacy 5DX system) couldn't inspect with high repeatability. The present invention assists in autofocus of the PCB and widens the joint inspection coverage. The present invention acts as a fast board tuning used model. Furthermore, the present invention improves V810's system architecture existing performance by either supplying accurate board height information or narrowing down current autofocus's search range.

The present invention provides a larger field of view resulting in more information which is collected to analyze the height reference that has accuracy advantage over the laser which is in point form. Furthermore, the setup time for the present invention is faster than laser mapping. The present invention provides a method to improve system call rate and test coverage for the automated x-ray inspection (AXI) machine. Particularly, the present invention can be employed for inspection & testing automation in the field of electronics, automotive industry, aerospace and defense, consumer electronic and communication industries. The present invention saves computing and PSP inspection time when the global surface model for conducting the full board profile is not needed. The present invention capitalizes on the advantages of PSP hardware mapping, 3D surface modeling and the autofocus technology. Moreover, the present system of the invention handles current V810 out of focus issues.

The one or more arrangements indicated in the previously mentioned embodiments and the present invention applied to the circuit boards are recited for example only and are not limited to the scope of the claim of the present invention. Any other equal or interchangeable elements should be included in the claim of the present invention.

Accordingly, while there has been shown and described the preferred embodiment of the invention is to be appreciated that the invention may be embodied otherwise than is herein specifically shown and described and, within said embodiment, certain changes may be made in the form and arrangement of the parts without departing from the underlying ideas or principles of this invention within the scope of the claims appended herewith.

We claim:

1. An automated X-ray inspection system employing phase shift profilometry (PSP) and three dimensional (3D) surface modeling for improving inspection of an object, said system comprising:
at least one projector for projecting light to said object, said at least one projector comprising a projector lens;
at least one optical lens for imaging a light pattern obtained from said object to at least one camera, said at least one camera being adapted to capture a plurality of images of said object;
wherein light passing from said projector lens of said at least one projector illuminates said object thereby generating said light pattern to be imaged from said object to said at least one camera via said at least one optical lens;
a calibration plate for calibrating a plurality of parameters of said object; and
a 3D surface interpolator to evaluate height information associated with said object and generate a complete surface profile of said object.

2. The system as claimed in claim 1, wherein said plurality of parameters comprises height, position, and magnification.

3. The system as claimed in claim 1, wherein said at least one projector is configured to project at least one of a fringe pattern to said object and a structured white light pattern to said object.

4. The system as claimed in claim 1, wherein said 3D surface interpolator is a global surface model (GSM) to inspect said object and said global surface model (GSM) use a thin-plate spline (TPS) method for evaluating surface interpolation of said object.

5. The system as claimed in claim 1, wherein said 3D surface interpolator is a Local Surface Model (LSM) to inspect said object and said Local Surface Model (LSM) use Predictive Slice Height (PSH) to estimate a z-height of at least one of a particular joint and solder of said object by taking an average z-height value of all its close neighbor focused joints for evaluating surface interpolation of said object.

6. The system as claimed in claim 1, wherein said at least one projector is a Pico Projector or equivalent means.

7. The system as claimed in claim 6, wherein said at least one pico-projector is implemented by DLP (digital light processing) technology.

8. The system as claimed in claim 1, wherein said at least one optical lens comprises a fixed-focus lens.

9. The system as claimed in claim 8, wherein means for focusing are arranged telecentrically with respect to said structured white light pattern.

10. The system as claimed in claim 9, wherein said means for focusing are a fixed focal length operative to provide at least one image of structured white light pattern from said object to said at least one camera.

11. The system as claimed in claim 1, wherein said system further comprises a data processing device for computing a plurality of phase shift values of said object with respect to a reference plane.

12. The system as claimed in claim 11, wherein said data processing device comprises a memory to collect said plurality of phase shift values of said object and a processor comprising at least one module to determine and measure surface profile of at least one object for a plurality of preselected regions.

13. The system as claimed in claim 12, wherein said measured surface profile of said at least one object for said plurality of preselected regions is provided to said 3D surface interpolator for interpolation and generating a global board warpage matrix.

14. The system as claimed in claim 1, wherein a partial surface profile of said object and/or said complete surface profile of said object are provided for reconstructing and generating a plurality of 3D image slices by utilizing tomosynthesis.

15. The system as claimed in claim 1, wherein said object is a PCB and said at least one camera operates in line scan mode or area scan mode.

16. A method for improving inspection of an object by an automated X-ray inspection system employing phase shift profilometry (PSP) and three dimensional (3D) surface modeling, said method comprising the steps of:
projecting light from at least one projector comprising a projector lens to said object;
imaging a light pattern obtained from said object by employing at least one optical lens to at least one camera for capturing a plurality of images of said object;
wherein light passing from said projector lens of said at least one projector illuminates said object thereby generating said light pattern to be imaged from said object to said at least one camera via said at least one optical lens;
calibrating a plurality of parameters of said object by a calibration plate; and
evaluating height information associated with said object by a 3D surface interpolator and generating a complete surface profile of said object.

17. The method as claimed in claim 16, wherein said plurality of parameters comprises height, position, and magnification.

18. The method as claimed in claim 16, wherein method further comprises projecting a structured white light pattern from said at least one projector to said object.

19. The method as claimed in claim 16, wherein said method further comprised arranging means for focusing telecentrically with respect to said structured white light pattern.

20. The method as claimed in claim 19, wherein said means for focusing are a fixed focal length operative for providing at least one image of structured white light pattern from said object to said at least one camera.

21. The method as claimed in claim 16, wherein said method further comprises computing a plurality of phase shift values of said object with respect to a reference plane by employing a data processing device.

22. The method as claimed in claim 21, wherein said method further comprises collecting said plurality of phase shift values of said object in a memory, and determining and measuring surface profile of at least one object for a plurality of preselected regions by a processor comprising at least one module.

23. The method as claimed in claim 22, wherein said method further comprises providing said measured surface profile of said at least one object for said plurality of preselected regions to said 3D surface interpolator for interpolation and generating a global board warpage matrix.

24. The method as claimed in claim 23, wherein said 3D surface interpolator is a global surface model (GSM) to inspect said object and said global surface model (GSM) use a thin-plate spline (TPS) method for evaluating surface interpolation of said object.

25. The method as claimed in claim 23, wherein said 3D surface interpolator is a Local Surface Model (LSM) to inspect said object and said Local Surface Model (LSM) use Predictive Slice Height (PSH) to estimate a z-height of at least one of a particular joint and solder of said object by taking an average z-height value of all its close neighbor focused joints for evaluating surface interpolation of said object.

26. The method as claimed in claim 16, wherein said method further comprises providing said complete surface profile of said object for reconstructing and generating a plurality of 3D image slices by utilizing tomosynthesis.

27. The method as claimed in claim 16, wherein said method further comprises operating said at least one camera in line scan mode or area scan mode.

\* \* \* \* \*